(12) United States Patent
Noda et al.

(10) Patent No.: US 8,343,124 B2
(45) Date of Patent: Jan. 1, 2013

(54) ABSORBENT ARTICLE

(75) Inventors: Yuki Noda, Kagawa (JP); Kenichiro Kuroda, Kagawa (JP)

(73) Assignee: Unicharm Corporation, Ehime (JP)

( * ) Notice: Subject to any disclaimer, the term of this patent is extended or adjusted under 35 U.S.C. 154(b) by 94 days.

(21) Appl. No.: 12/746,427

(22) PCT Filed: Dec. 4, 2008

(86) PCT No.: PCT/JP2008/072020
§ 371 (c)(1),
(2), (4) Date: Aug. 24, 2010

(87) PCT Pub. No.: WO2009/072545
PCT Pub. Date: Jun. 11, 2009

(65) Prior Publication Data
US 2010/0305541 A1    Dec. 2, 2010

(30) Foreign Application Priority Data
Dec. 5, 2007  (JP) .............................. P2007-315096

(51) Int. Cl.
*A61F 13/15* (2006.01)

(52) U.S. Cl. ......... 604/385.03; 604/385.01; 604/385.02; 604/385.04; 604/385.05; 604/385.14; 604/385.16; 604/387

(58) Field of Classification Search ............. 604/385.22, 604/385.16, 385.01, 385.02, 385.03, 385.05, 604/387, 385.14
See application file for complete search history.

(56) References Cited

U.S. PATENT DOCUMENTS

| 5,611,790 A * | 3/1997 | Osborn et al. ................ 604/391 |
| 6,042,575 A * | 3/2000 | Osborn et al. ................ 604/387 |
| 7,125,401 B2 | 10/2006 | Yoshimasa |
| 2005/0015068 A1 * | 1/2005 | Bean et al. ............... 604/385.16 |

FOREIGN PATENT DOCUMENTS
CN   1432351   7/2003

OTHER PUBLICATIONS
Chinese Office Action for Application No. 200880119413.4 mailed May 31, 2012.

* cited by examiner

*Primary Examiner* — Lynne Anderson
*Assistant Examiner* — Bradley Philips
(74) *Attorney, Agent, or Firm* — Lowe Hauptman Ham & Berner, LLP

(57) ABSTRACT

An absorbent article including an absorbent article main body which is extended in a longitude direction and having a front end portion and a rear end portion, and which includes an absorber of liquid-retaining, a topsheet of liquid-permeable covering a surface of the absorber, and a backsheet of liquid-nonpermeable supporting the absorber from a back surface of the absorber, the absorbent article includes: a belt-shaped member extended in the longitude direction of the absorbent article main body, including a base end portion fixed to any one of the absorber and the backsheet and a tip portion not fixed, and being stretchable in the longitude direction; and an attaching sheet provided on a back surface of the belt-shaped member and configured to be attached to clothing, wherein the attaching sheet is extended in a width direction of the belt-shaped member and both end portions of the attaching sheet are fixed to the belt-shaped member.

14 Claims, 7 Drawing Sheets

ABSORBENT ARTICLE

RELATED APPLICATIONS

The present application is national phase of International Application Number PCT/JP2008/072020, filed Dec. 4, 2008, and claims priority from, Japanese Application Number 2007-315096, filed Dec. 5, 2007, the disclosures of which are hereby incorporated by reference herein in their entirety.

TECHNICAL FIELD

The present invention relates to an absorbent article such as a sanitary napkin.

BACKGROUND ART

There has heretofore been known an absorbent article such as a sanitary napkin which is provided with an adhesive part formed on a back surface of the strip-shaped and is used by having the adhesive part attached to the crotch portion of underwear.

Japanese Patent Application Publication No. Hei 11-99179 describes the following sanitary napkin as an example of such an absorbent article. Specifically, in the sanitary napkin, an elastic flap (elastic member) stretchable in the front and rear direction is provided so as to protrude from each of front and rear end portions of the napkin, and an adhesive part to be attached to underwear is formed on the back of a tip portion of the elastic flap.

Patent Document 1: Japanese Patent Application Publication No. Hei 11-99179

However, in the absorbent article as described above, when the elastic flap extended from the rear end portion is positioned near the cleavage of the buttocks, the flap deforms along the cleavage into a cross-sectionally triangular shape and the adhesive part formed on the flap also deforms into a cross-sectionally triangular shape.

Meanwhile, underwear that is not particularly very tight, such as shorts for everyday wear, deforms into a cross-sectionally triangular shape together with the elastic flaps immediately after the underwear is fitted to the body, but tends to return to its original flat shape when the wearer moves her body.

As a result, the adhesive parts are peeled off from the underwear near the cleavage and thus the elastic flaps come off from the underwear. Consequently, leakage of body fluid such as leakage of menstrual blood, for example, may occur due to a gap between the napkin and the body (particularly, the buttocks) or slippage of the napkin. Alternatively, when adhesion between the elastic flaps and the underwear is strong, the flaps may move away from the buttocks and the body fluid may leak from a gap therebetween.

DISCLOSURE OF THE INVENTION

Against this background, it is an object of the present invention to provide an absorbent article which is securely fixed to underwear even near the buttocks and thus has no risk of leakage of body fluid and the like.

According to a first aspect of the present invention, provided is an absorbent article including an absorbent article main body which is extended in a longitudinal direction and having a front end portion and a rear end portion, and which includes an absorber of liquid-retaining, a topsheet of liquid-permeable covering a surface of the absorber, and a backsheet of liquid-nonpermeable supporting the absorber from a back surface of the absorber, the absorbent article includes: a belt-shaped member extended in the longitude direction of the absorbent article main body, including a base end portion fixed to any one of the absorber and the backsheet and a tip portion not fixed, and being stretchable in the longitude direction; and an attaching sheet provided on a back surface of the belt-shaped member and configured to be attached to clothing, wherein the attaching sheet is extended in a width direction of the belt-shaped member and both end portions of the attaching sheet are fixed to the belt-shaped member.

BEST MODES FOR CARRYING OUT THE INVENTION

Figure 1:
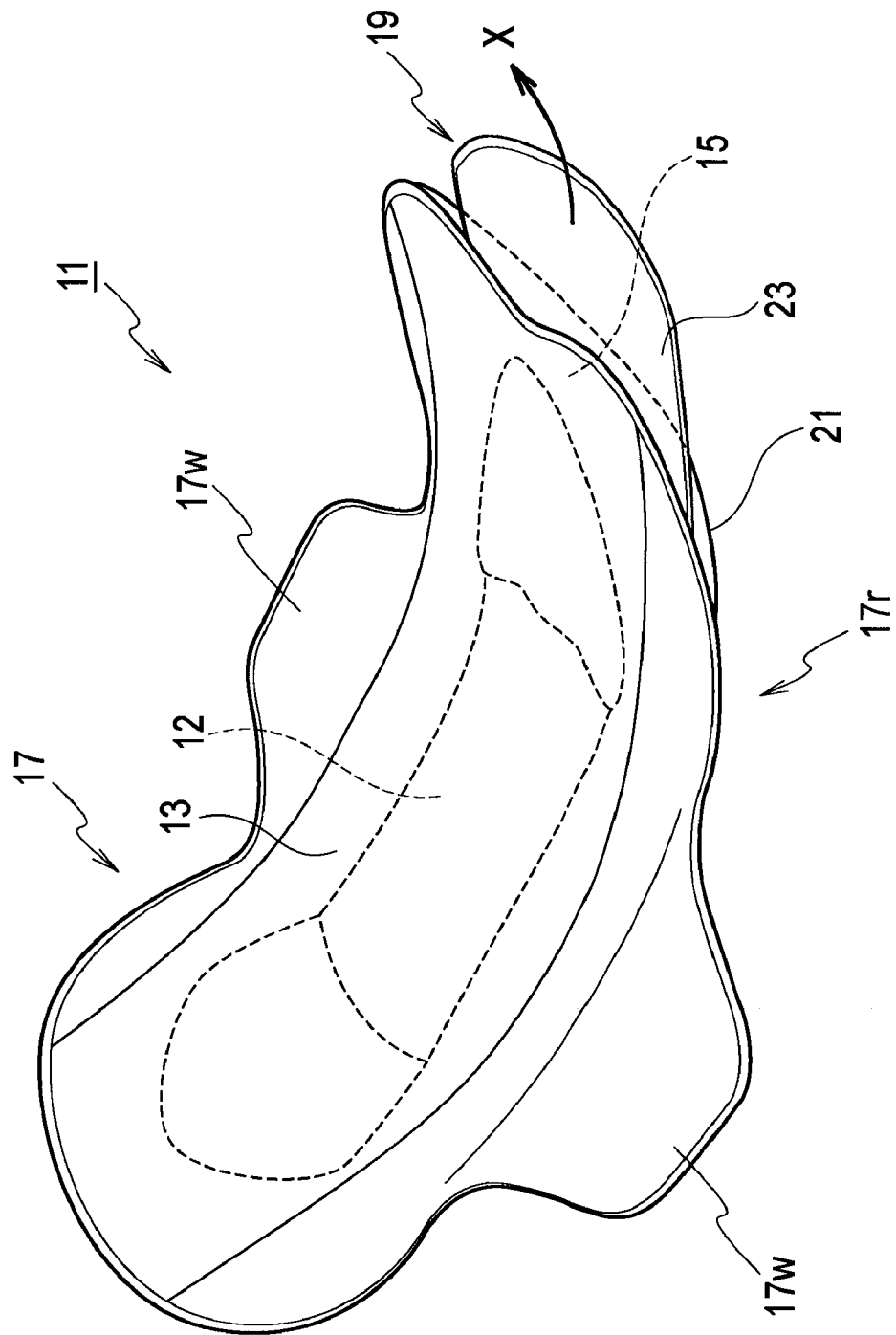
FIG. 1 is a perspective view of a sanitary napkin that is an embodiment of an absorbent article according to the present invention.

An absorbent article according to the present invention includes a belt-shaped member and an attaching sheet in an absorbent article main body (which may hereinafter be simply referred to as "main body") including a topsheet of liquid-permeable positioned on a skin contact surface, a backsheet of liquid-nonpermeable positioned on a clothing contact surface and an absorber interposed between the sheets. Specifically, the belt-shaped member is extended in the same direction as the main body, and the attaching sheet is provided on a back surface of the belt-shaped member and attaches the main body to clothing.

The main body is extended in the longitude direction and has a front end portion and a rear end portion. Note that, in this specification, when the is in use, a region positioned on the stomach side of a user is called the front end portion, and a region positioned on the buttocks side of the user is called the rear end portion.

The belt-shaped member has its one end (base end portion) fixed to the main body. Specifically, the belt-shaped member has the base end portion that is fixed to the main body, and a tip portion that is not fixed. The region fixed to the main body may be on the back (backsheet) of the main body or may be on the back (backsheet side) of the absorber.

At least a part of the belt-shaped member is stretchable in the longitude direction with respect to the main body. Thus, in use, the belt-shaped member can support and elastically raise the absorber or the main body (which may hereinafter be collectively described as "main body"), so that the main body is properly attached to the body side.

It is preferable that the belt-shaped member is stretchable to the extent that the tip portion of the belt-shaped member can be extended beyond the rear end portion of the main body.

It is also preferable that the belt-shaped member can be pulled out in the longitude direction with respect to the main body, and that, in a state before use, the tip portion of the belt-shaped member protrudes beyond the rear end portion of the main body on the pull-out direction side, and forms a grip part at the time of the pull-out.

Here, the strip shape means a substantially oblong shape. Therefore, a specific shape of the belt-shaped member is not limited to a rectangular shape or the like. For example, an interval in a width direction need not be fixed and may be narrower in the central portion in the longitude direction, or both sides may be curved.

Moreover, it is preferable that the belt-shaped member has a predetermined length sufficient to support the main body. To be more specific, it is preferable that the belt-shaped member has a length not less than ½ of the length of the main body (or the backsheet), and that the base end portion of the belt-shaped member is fixed at a position shifted toward the front end portion from the central portion in the longitude direction of the main body (or the backsheet).

Furthermore, it is preferable that an absorbent member is provided on a surface (skin contact surface) of the belt-shaped member so that the body fluid can be absorbed also in the belt-shaped member. It is more preferable that the absorbent member is provided on the surface of the belt-shaped member, which is extended from the main body when in use.

The attaching sheet is extended in the width direction of the belt-shaped member, and both sides of the attaching sheet are fixed on at least two points in the width direction of the belt-shaped member. Specifically, the attaching sheet is connected to the belt-shaped member only at both side edges in the longitude direction of the attaching sheet. Therefore, other than both the side edges, the attaching sheet is separable from the belt-shaped member and thus can freely come into contact with and separate from the belt-shaped member.

It is preferable to fix the attaching sheet at two points on the tip portion side of the belt-shaped member, which is not fixed to the main body, on a portion extended from the rear end portion of the main body when in use.

The attaching sheet preferably includes a support sheet fixed at a predetermined position on the tip portion side of the belt-shaped member, and an attaching member formed of, for example, an adhesive material formed on the support sheet. The support sheet is extended in the width direction of the belt-shaped member and both end portions of the support sheet are fixed to the belt-shaped member.

With reference to the accompanying drawings, embodiments of the absorbent article according to the present invention will be described in more detail below. The following embodiments are only examples, and the technical scope of the present invention is not limited to these exemplary embodiments.

FIG. 1 is a perspective view of a sanitary napkin (which may hereinafter be simply referred to as "napkin") 11 that is an embodiment of an absorbent article according to the present invention.

As shown in FIG. 1, the sanitary napkin 11 consists of a strip-shaped absorbent article main body (main body) 17 including a liquid-retaining absorber 12, a topsheet 13 of liquid-permeable covering a surface of the absorber 12, and a backsheet 15 of liquid-nonpermeable supporting the absorber 12 from the back.

On both sides of the main body 17, right and left wings 17w and 17w are formed to assist fixing of the sanitary napkin 11 to underwear. On the backsheet 15 of each of the right and left wings 17w and 17w, an attaching part (not shown) like an adhesive part for fixing the main body 17 to the underwear when the sanitary napkin is used is formed. Furthermore, similar attaching parts for fixing the main body 17 to the underwear when the sanitary napkin is used may be formed in any portion such as a front end portion, a central portion and the like of the main body 17.

On a back surface 17r of the main body 17, a strip-shaped support means 19 including a belt-shaped member 23 and an attaching sheet to be described later is provided for supporting the main body 17 when the sanitary napkin is used. The strip-shaped support means 19 can be pulled out backward (arrow X) in the longitude direction of the main body.

More details are as follows.

Figure 2:
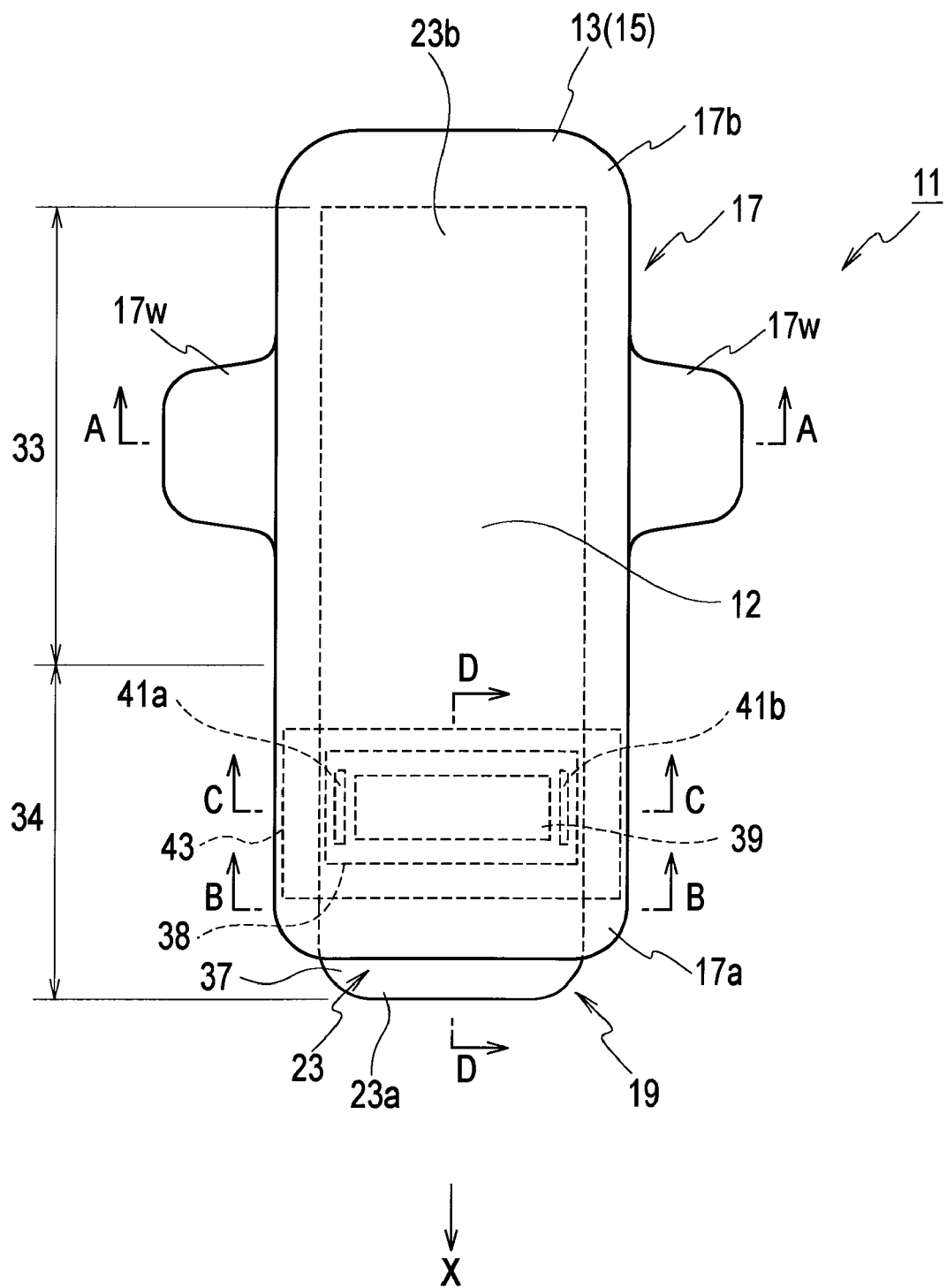
FIG. 2 is a plan view when the sanitary napkin shown in FIG. 1 is stretched out flat.
Figure 3A:
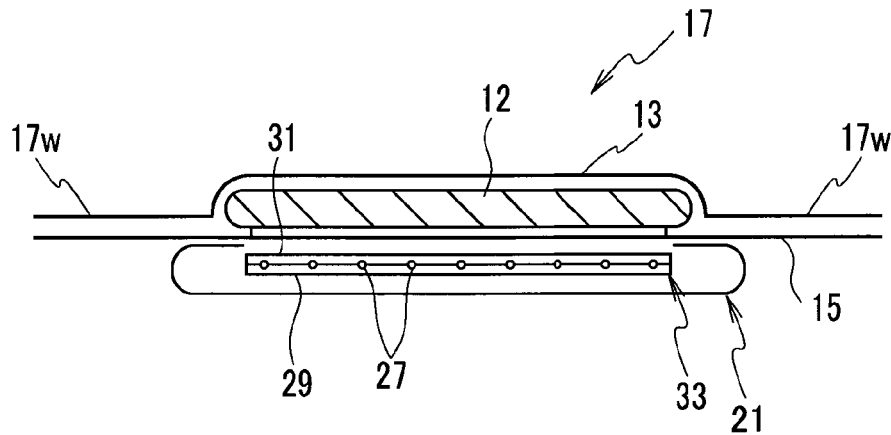
FIG. 3(A) is a cross-sectional view taken along the line A-A in FIG. 2.
Figure 3B:
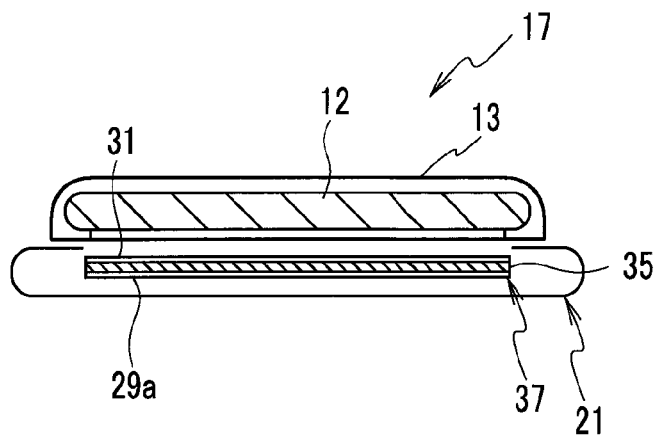
FIG. 3(B) is a cross-sectional view taken along the line B-B in FIG. 2.
Figure 3C:
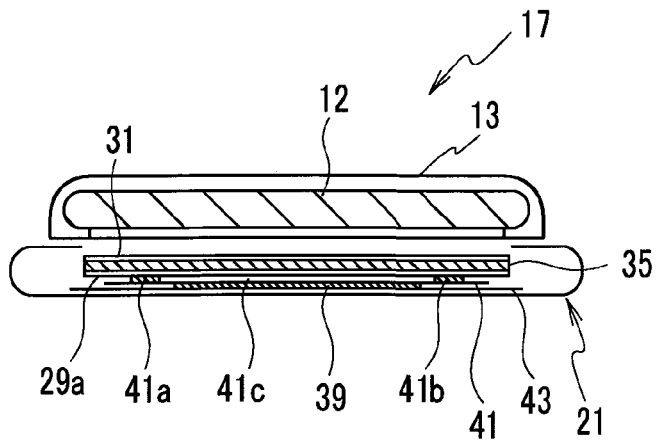
FIG. 3(C) is a cross-sectional view taken along the line C-C in FIG. 2.

FIG. 2 is a plan view when the napkin 11 shown in FIG. 1 is stretched out flat. FIG. 3(A) is a cross-sectional view taken along the line A-A in FIG. 2, FIG. 3(B) is a cross-sectional view taken along the line B-B in FIG. 2, and FIG. 3(C) is a cross-sectional view taken along the line C-C in FIG. 2.

As shown in FIG. 2, the strip-shaped support means 19 includes the belt-shaped member 23 which can be pulled out in the longitude direction of the main body 17, and an attaching sheet 38 which is provided on a back surface of the belt-shaped member 23 and attaches the main body 17 to the underwear.

The belt-shaped member 23 has a length not less than ½ of the length of the main body 17 (or the backsheet 15) in the longitude direction. Moreover, a tip portion 23a of the belt-shaped member 23 protrudes from a rear end portion 17a of the main body 17, and a base end portion 23b of the belt-shaped member 23 is fixed at a predetermined position near a front end portion 17b of the main body 17.

A length in the width direction of the belt-shaped member 23 is preferably 30 to 150%, more preferably 60 to 130% of the length in the width direction of the main body 17 (or the backsheet 15).

As shown in FIG. 2 and FIGS. 3(A) and 3(B), the belt-shaped member 23 includes a stretchable stretch part 33 and a non-stretch part 34 disposed behind and adjacent to the stretch part 33. A tip portion of the non-stretch part 34 forms a grip part 37 which functions as a knob at the time of pull-out. Thus, stretchability of the belt-shaped member in the front-back (longitude) direction of the main body allows the main body be attached more securely to the body side.

As shown in FIG. 3(A), the stretch part 33 has an elastic body (elastic member) 27 like rubber (elastic body), and base materials 29 and 31 sandwiching the elastic body 27 therebetween. As shown in FIG. 3(B), the grip part 37 has a non-stretchable absorbent member 35 and base materials 29a and 31 sandwiching the absorbent member 35 therebetween.

As a stretchable range of the stretch part of the belt-shaped member, the overall length of the belt-shaped member when stretched is preferably 105 to 300%, more preferably 110 to 180% of the overall length when not stretched. Hence, the belt-shaped member can elastically raise the main body and properly push up and attach the main body to the body side. Furthermore, elastic body stress at the stretch ratio of 105 to 300% is preferably within a range of 5 to 100 cN/25 mm, more preferably within a range of 20 to 80 cN/25 mm.

As shown in FIG. 2 and FIG. 3(C), on a back surface (clothing contact surface) of a region of the non-stretch part 34 of the belt-shaped member 23, the region being adjacent to the grip part 37, the attaching sheet 38 is provided for attaching the belt-shaped member 23 on the underwear when the napkin is used. The attaching sheet 38 consists of an adhesive part 39 and a support sheet 41 for supporting the adhesive part, and is fixed to the back surface of the non-stretch part at both end portions 41a and 41b of the support sheet. A peel-off sheet 43 for protecting the adhesive part 39 up to the point of use is attached to the attaching sheet 38 including the adhesive part 39.

As shown in FIG. 1 and FIGS. 3(A) to 3(C), on the back surface 17r of the main body 17, a cylindrical guide means 21 for guiding pull-out of the belt-shaped member 23 (or the strip-shaped support means 19) is provided by being fixed to the backsheet 15. The belt-shaped member 23 is disposed inside the cylindrical guide means 21. This configuration can prevent the belt-shaped member from hanging downward from the back surface of the main body. Note that the cylindrical guide means may be disposed so as to cover almost the entire area of the main body, or may be disposed only in the vicinity of the rear end of the main body. The disposition of the cylindrical guide means at least in the vicinity of the rear end of the main body eliminates a risk of a positional shift in the main body due to excessive sliding of the belt-shaped member in the width direction.

To be more specific, the longitude dimension of the cylindrical guide means is preferably 10 to 100%, more preferably 50 to 90% of the longitude dimension of the main body. The transverse dimension of the cylindrical guide means is preferably 100 to 200%, more preferably 105 to 150% of the transverse dimension of the belt-shaped member.

When using the sanitary napkin having the above configuration, first, the front end portion 17b and central portion of the main body as well as the attaching parts (not shown) provided on the right and left wings 17w and 17w are fixed to front and central parts of the underwear. Next, by holding the grip part 37, the rear end portion 23a of the belt-shaped member 23 is pulled out backward (arrow X direction) against the tension of the stretch part 33. Thus, the peel-off sheet 43 is peeled off and the adhesive part 39 of the attaching sheet 38 is exposed. Accordingly, the exposed adhesive part 39 is fixed to a rear part of the underwear. In this way, the underwear may be pulled up after the napkin is completely fixed to the underwear. Alternatively, when the underwear is pulled up after the napkin is fixed to the front and central parts of the underwear, the grip part 37 may be pulled out by reaching into the underwear from the back side. Thus, the adhesive part 39 can be fixed to the rear part of the underwear.

When the absorbent article main body is fixed to the underwear as described above, the main body 17 when the napkin is used is supported in front and rear regions of the underwear while being biased toward the body by the elasticity of the stretch part 33.

Therefore, even when the central part and the like of the underwear are loosened after the napkin is attached, no gap is caused between the surface of the main body and the body. Thus, leakage of body fluid or the like does not occur.

Moreover, in this embodiment, the absorbent member 35 is formed in the non-stretch part (including the grip part 37) which is pulled out from the rear end portion 17a of the main body. Therefore, in use, even if the body fluid or the like leaks from the rear end portion 17a of the main body, the leaked body fluid can be absorbed by the absorbent member 35. Moreover, the absorbent member imparts rigidity to the grip part and thus can prevent the grip part from being deformed by twisting and the like during the pull-out or during use.

With reference again to FIG. 3(C), as described above, the support sheet 41 which constitutes the attaching sheet 38 is extended in the width direction (horizontal direction in FIG. 3(C) of the belt-shaped member 23, and both the end portions 41a and 41b are fixed near both the sides (two points in the width direction) of the tip region of the belt-shaped member 23. Therefore, between both the end portions 41a and 41b, a gap 41c is formed between the belt-shaped member 23 and the support sheet 41 (attaching sheet). Accordingly, the support sheet 41 is separable from (can freely come into contact with and separate from) the belt-shaped member 23. A length in the width direction of the gap 41c is preferably 30 to 95%, more preferably 50 to 90% of the length in the width direction of the belt-shaped member 23.

Figure 4:
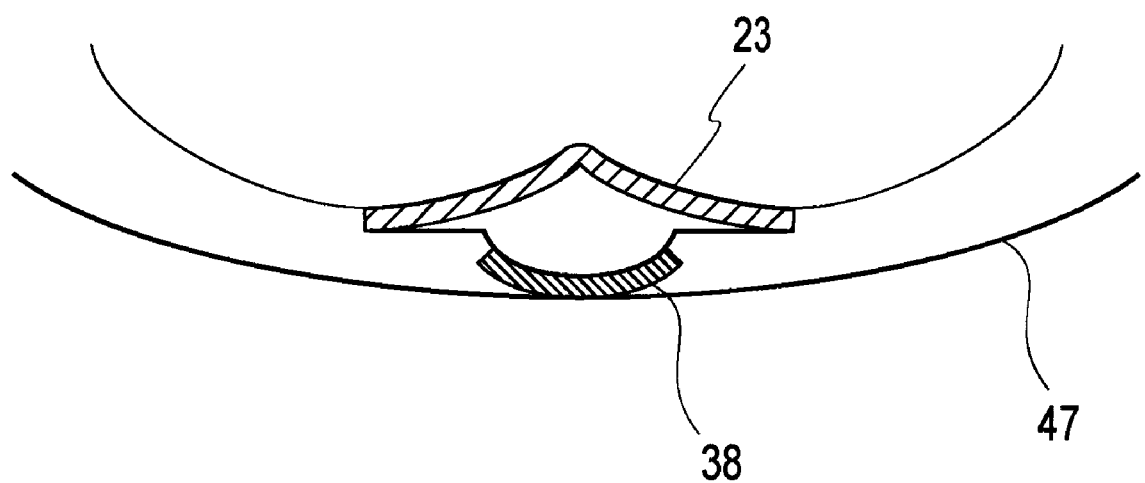
FIG. 4 is a conceptual diagram showing an effect of an attaching sheet.

FIG. 4 is a conceptual diagram showing an effect of the attaching sheet 38 described above.

When in use, the belt-shaped member 23 is pulled out backward from the main body 17 and the attaching sheet 38 is fixed to the rear part of underwear 47. Hence, the attaching sheet 38 is positioned at the cleavage of the buttocks. Accordingly, the belt-shaped member 23 adjacent to the attaching sheet 38 fits in the cleavage and forms a cross-sectionally triangular shape as shown in FIG. 4. Meanwhile, the attaching sheet 38 is not fixed to and is separable from the belt-shaped member 23 in the central portion in the width direction as described above. Thus, the attaching sheet 38 maintains the flat shape as it is fixed to the underwear. In other words, the belt-shaped member 23 deformed into the cross-sectionally triangular shape is separated from the attaching sheet 38.

Therefore, the attaching sheet 38 does not come off from the underwear 47 by being pulled by the belt-shaped member 23 while the user is moving his/her body. Thus, the positional shift in the absorbent article main body or the leakage of body fluid can be prevented. Moreover, the attaching sheet does not come off and is securely fixed to the underwear. Thus, the belt-shaped member 23 can be prevented from being abnormally deformed while the napkin is used, and the sanitary napkin itself can be prevented from being shifted in position or abnormally deformed while the napkin is used. Furthermore, by keeping the belt-shaped member 23 with the absorbent member 35 fitted to the cleavage along the buttocks while the attaching sheet 38 is fixed to the underwear, leakage of the body fluid in the back region can also be surely absorbed.

Figure 5A:
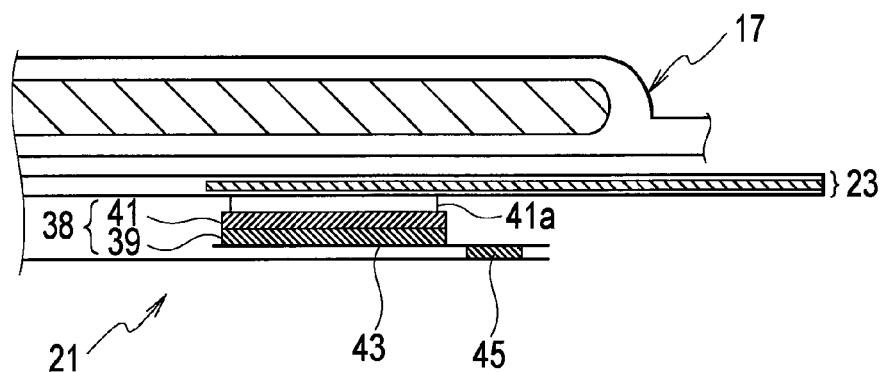
FIGS. 5(A) and 5(B) are cross-sectional views taken along the line D-D in FIG. 2.
Figure 5B:
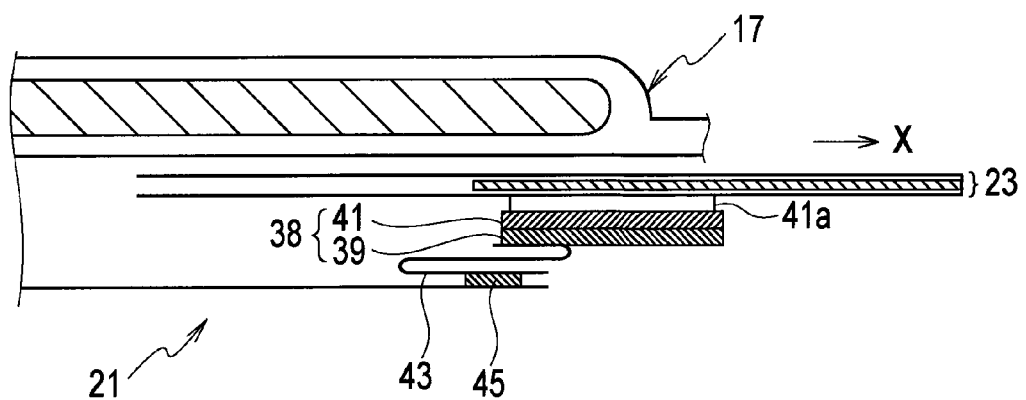

FIG. 5(A) is a cross-sectional view taken along the line D-D in FIG. 2.

As shown in FIG. 5(A), the peel-off sheet 43 covering the adhesive part 39 of the attaching sheet 38 has a peel-off sheet protrusion 43a extended from the adhesive part 39 backward (forward in the pull-out direction of the belt-shaped member). This peel-off sheet protrusion 43a is fixed to the rear end portion of the cylindrical guide means 21. In other words, the peel-off sheet 43 is fixed to the cylindrical guide means 21 behind the adhesive part 39.

Therefore, when the belt-shaped member 23 is pulled out backward in use, the peel-off sheet 43 is peeled off from the adhesive part 39 using a fixed portion 45 fixing the peel-off sheet 43 to the cylindrical guide means 21 as a starting point, and the adhesive part 39 is exposed. Thus, when pulling out the belt-shaped member 23 and fixing the adhesive part 39 to a predetermined portion on the underwear, the adhesive part 39 can be easily attached to an intended portion.

As the liquid-retaining absorber 12, the topsheet 13 of liquid-permeable covering the surface of the absorber, and the backsheet 15 of liquid-nonpermeable supporting the absorber from the back, which constitute the main body 17, heretofore known materials are used and are not particularly limited.

As the cylindrical guide means 21, heretofore known materials and the like can be used as in the case of the topsheet 13 and backsheet 15.

As the base materials 29 and 31 (see FIG. 3(A)) of the stretch part of the belt-shaped member 23, liquid-permeable sheets, which can be used as the topsheet, can be preferably used. As the elastic body (elastic member) 27, natural rubber, polyurethane elastic yarn and the like can be used. Alternatively, fibrous sheets containing elastomer resin may be used as the base materials of the stretch part. In such a case, stretching properties are more easily imparted by embossing the base materials of the stretch part in a wave pattern.

As the base material 29a (see FIGS. 3(B) and 3(C)) on the back side of the non-stretch part, a liquid-nonpermeable material is preferably used as in the case of the backsheet described above. As the absorbent member 35 arbitrarily provided on the base material 29a, heretofore known materials can be used as in the case of the absorber 12. Note that, as the base material 31, a liquid-absorbing material may be used and be configured to also serve as the absorbent member.

As the support sheet of the attaching sheet 38, a heretofore known material and the like can be used as in the case of the backsheet 15, for example.

As the adhesive material of the attaching sheet 38, heretofore known materials can be used, such as, but not particularly limited to, water-soluble polymer, bridging material, plasticizer and gel adhesive made of water.

Moreover, instead of the adhesive, a hot-melt adhesive can also be used. Since the hot-melt adhesive preferably has tackiness at normal temperature, a pressure sensitive adhesive is cited as a preferred example.

The present invention is not limited to Embodiment 1 described above, and various modifications can be made thereto.

Figure 6:
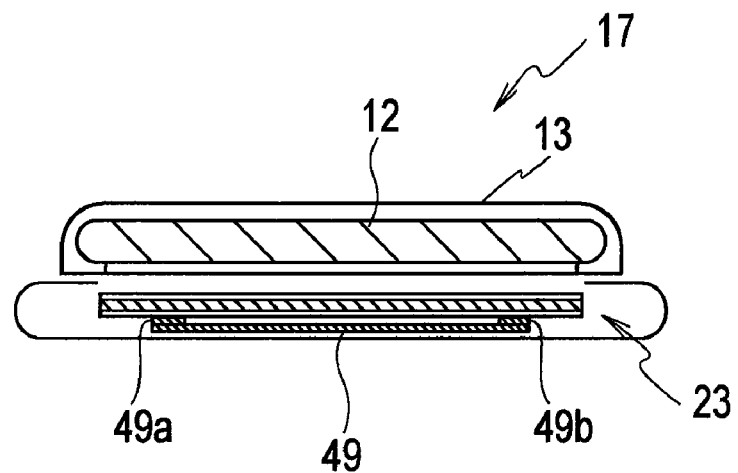
FIG. 6 is a cross-sectional view in the width direction of a sanitary napkin that is another embodiment of the absorbent article according to the present invention.

For example, in Embodiment 1, the attaching sheet 38 consists of the support sheet 41 fixed to the belt-shaped member and the adhesive part 39 formed on the support sheet 41. However, as shown in FIG. 6, a hook material (mechanical hook material) 49 can be used instead.

Also in this case, for example, the hook material 49 as the attaching sheet 38 is extended in the width direction of the belt-shaped member 23, and both end portions 49a and 49b are fixed near both sides (two points in the width direction) of the belt-shaped member 23. Other than both the end portions 49a and 49b, the hook material 49 freely comes into contact with and separates from the belt-shaped member 23.

Therefore, similarly in the attaching sheet of this embodiment, the attaching sheet fixed to the underwear and the belt-shaped member positioned at the cleavage of the buttocks can freely come into contact with and separate from each other in the central portion of the attaching sheet. Thus, the belt-shaped member can be fitted to the buttocks while the attaching sheet is fixed to the underwear. As a result, a gap between the absorbent article main body and the body can be prevented, and leakage of body fluid can be surely prevented.

Figure 7:
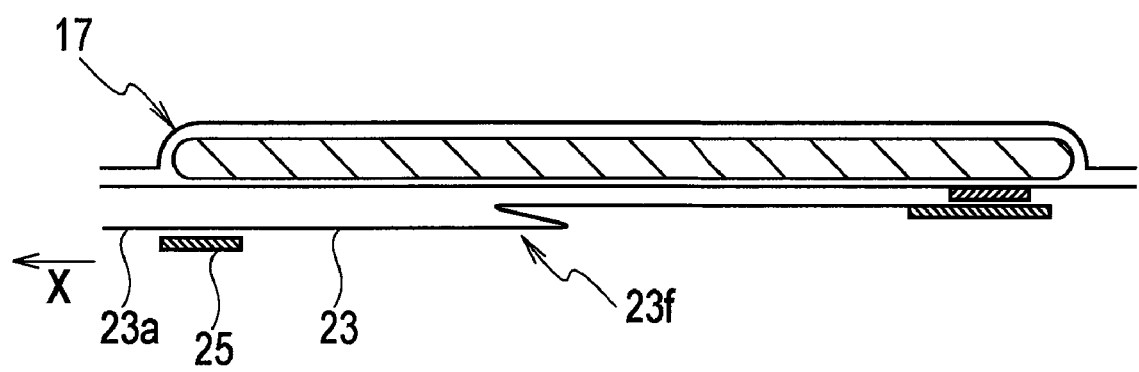
FIG. 7 is a cross-sectional view in the longitude direction of a sanitary napkin that is another embodiment of the absorbent article according to the present invention.
Figure 8:
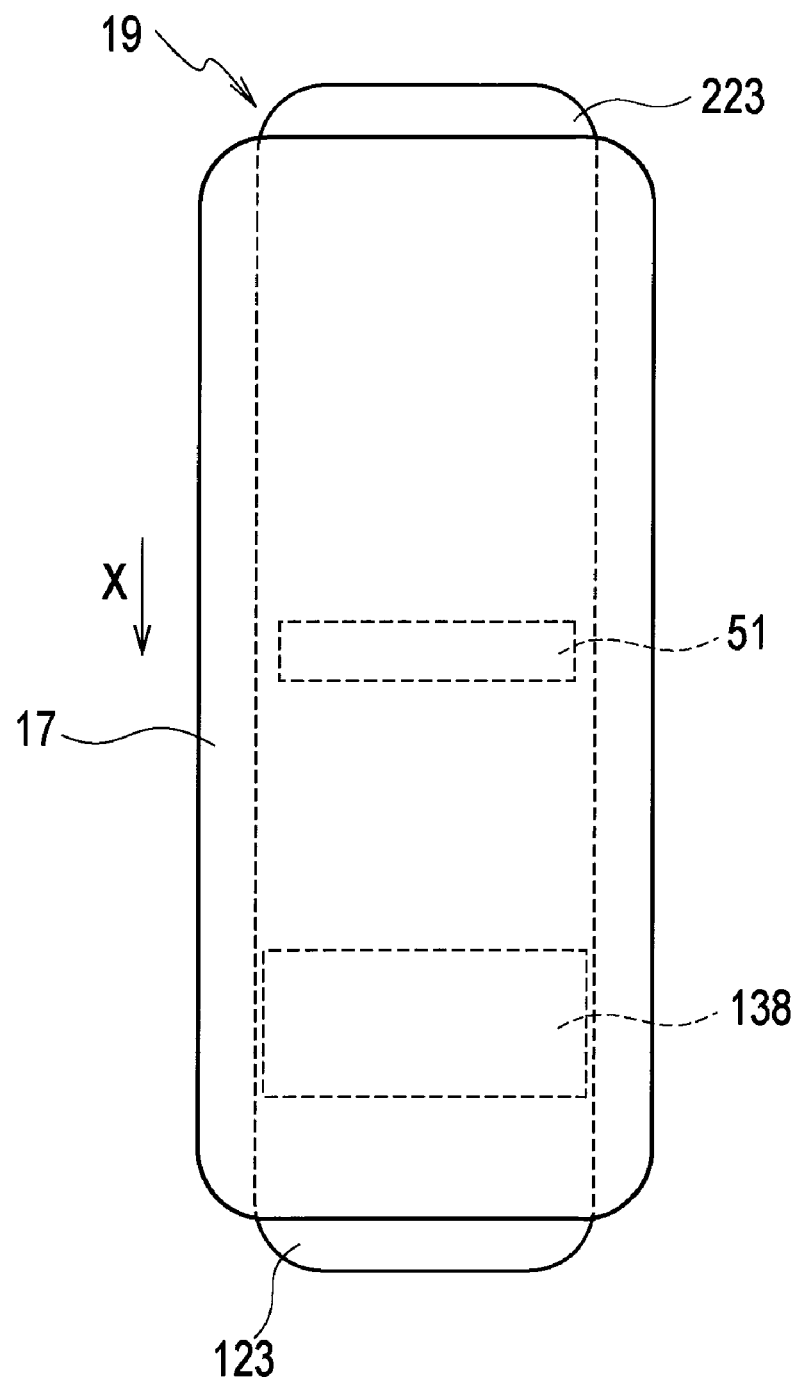
FIG. 8 is a plan view of a sanitary napkin that is another embodiment of the absorbent article according to the present invention.

Moreover, in Embodiment 1, the stretch part 33 of the belt-shaped member 23 includes the elastic body 27 sandwiched between the base materials 29 and 31. However, the stretch part of the present invention is not limited thereto but may, for example, stretch by having a folded portion 23f as shown in FIG. 7.

In the belt-shaped member 23 having the folded portion 23f, the folded portion 23f is stretched out by pulling out the tip portion 23a of the belt-shaped member 23 backward (in the arrow X direction) and thus the belt-shaped member 23 is pulled out from the main body 17.

Furthermore, in Embodiment 1, the belt-shaped member 23 protrudes in one direction (backward) from the absorbent article main body 17. However, the present invention is not limited thereto.

For example, the strip-shaped support means 19 can be fixed by a fixed part 51 in the central portion in the longitude direction of the main body 17, and can have a forward belt-shaped member 223 extended forward relative to the fixed part 51 and a backward belt-shaped member 123 extended backward relative to the fixed part 51. The backward belt-shaped member 123 has the same configuration as that of the belt-shaped member 23, and includes an attaching sheet (138) fixed to the backward belt-shaped member 123 on both end portions. As means for fixing the forward belt-shaped member 223 to the underwear, any means may be used and an attaching part (not shown) such as an adhesive part may be provided directly on the back surface of the belt-shaped member without using the attaching sheet.

In the absorbent article, the main body can be fixed to the underwear, for example, by pulling out the forward belt-shaped member 223 and fixing it to the underwear, while pulling out the backward belt-shaped member 123 and fixing the attaching sheet (138) provided therein to the underwear.

Also in this embodiment, the absorbent article can be securely fixed to the front and rear parts of the underwear. Even when the underwear is loosened after the absorbent article is attached, the main body 17 can be securely pressed against the body of the user. Therefore, leakage of body fluid while the absorbent article is used can be surely prevented.

Furthermore, in Embodiment 1, the cylindrical guide means 21 is disposed on the back surface of the main body to guide the pull-out of the belt-shaped member 23. However, the belt-shaped member 23 may be disposed between the backsheet 15 and the absorber 12 so that the backsheet serves as the cylindrical guide means. In this case, rear end portions of the backsheet and absorber are not connected to each other.

Alternatively, the backsheet or topsheet may be extended in the width direction and end portions may be connected to each other to form a cylindrical shape having an opening on the back side of the main body.

Note that the entire contents of Japanese Patent Application No. 2007-315096 (filed on Dec. 5, 2007) are incorporated herein by reference.

[Industrial Applicability]

In the absorbent article of the present invention, the attaching sheet is fixed to the belt-shaped member at both the end portions of the belt-shaped member, and is separable from the belt-shaped member at a portion other than both the end portions. As a result, even when the attaching sheet is positioned near the cleavage of the buttocks and the adjacent belt-shaped member is deformed along the cleavage into a cross-sectionally triangular shape, the attaching sheet can maintain its flat state along the underwear to which the sheet is attached.

Therefore, even if the posture of the user is changed while the napkin is used, the attaching sheet does not come off from the underwear at the cleavage or the belt-shaped member is not separated from the cleavage. Thus, the absorbent article is can be attached to the body without causing a gap between the absorbent article main body and the body. As a result, leakage of body fluid and the like due to the absorbent article being shifted or coming off from the underwear can be prevented.

The invention claimed is:
1. An absorbent article, comprising:
an absorbent article main body extending in a longitudinal direction of the absorbent article and having
a front end portion and rear end portion,
a liquid-retaining absorber,
a liquid-permeable topsheet covering a top surface of the absorber, and a liquid-impermeable backsheet supporting the absorber and opposite to the topsheet in a thickness direction of the absorbent article;

a belt-shaped member extending in the longitudinal direction and including a base end portion fixed to the absorber or the backsheet, and a tip portion not fixed to the absorber and the backsheet and stretchable in the longitude direction; and an attaching member provided on a back surface of the belt-shaped member and configured to be attached to clothing, in use, wherein the attaching member extends in a width direction perpendicular to the longitudinal direction and includes side portions opposite to each other in the width direction and fixed to the back surface of the belt-shaped member, and the attaching member is separate from, in the thickness direction, the belt-shaped member between the side portions.

2. The absorbent article according to claim 1, wherein the belt-shaped member has stretching properties and the tip portion of the belt-shaped member is extendable outwardly from the rear end portion of the absorbent article main body.

3. The absorbent article according claim 1, wherein the belt-shaped member is extendable outwardly from the absorbent article main body in the longitudinal direction, and a part of the tip portion of the belt-shaped member protrudes outwardly and beyond the rear end portion of the absorbent article main body in the longitudinal direction when the belt-shaped member is in a relaxed, non-extended state.

4. The absorbent article according to claim 1, wherein the belt-shaped member further comprises an absorbent member on the back surface thereof.

5. The absorbent article according to claim 1, wherein a dimension of the belt-shaped member in the longitudinal direction is at least half of the dimension of the absorbent article main body in the longitudinal direction, and the base end portion of the belt-shaped member is fixed at the front end portion forward from a central portion of the absorbent article main body in the longitude direction.

6. The absorbent article according to claim 1, wherein the attaching member defines a space between the belt-shaped member and the attaching member in the thickness direction and between the side portions in the width direction.

7. The absorbent article according to claim 1, wherein the belt-shaped member comprises an elastically stretchable part including the base end portion, and a non-elastically stretchable part including the tip portion.

8. The absorbent article according to claim 7, wherein the side portions of the attaching member are fixed to the back surface of the belt-shaped member in the non-elastically stretchable part.

9. The absorbent article according to claim 1, wherein the attaching member further comprises an adhesive part opposite to the belt-shaped member in the thickness direction and between the side portions of the attaching member in the width direction.

10. The absorbent article according to claim 9, further comprising a peel-off sheet directly attaching to the adhesive part of the attaching member and adapted to be peeled off before use.

11. The absorbent article according to claim 10, further comprising a guide member for guiding the belt-shaped member to be pulled outwardly in the longitudinal direction, wherein said guide member includes opposite edges fixed to the backsheet of the absorbent article main body.

12. The absorbent article according to claim 11, wherein the guide member supports and covers the belt-shaped member from below for preventing the belt-shaped member from hanging downward from the backsheet of the absorbent article main body.

13. The absorbent article according to claim 11, wherein the peel-off sheet is fixed to the guide member at a fixing portion adjacent to the adhesive part.

14. The absorbent article according to claim 1, wherein the attaching member includes a hook adapted to be directly attached to the clothing in use.

\* \* \* \* \*